United States Patent
Heismann

(10) Patent No.: US 7,196,331 B2
(45) Date of Patent: Mar. 27, 2007

(54) DETECTOR MODULE

(75) Inventor: Bjoern Heismann, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/033,516

(22) Filed: Jan. 12, 2005

(65) Prior Publication Data

US 2005/0161608 A1 Jul. 28, 2005

(30) Foreign Application Priority Data

Jan. 12, 2004 (DE) .................. 10 2004 001 688

(51) Int. Cl.
*G01T 1/20* (2006.01)

(52) U.S. Cl. .................................. 250/367

(58) Field of Classification Search ............. 250/367, 250/370.11, 361 R, 585, 580, 581, 582, 583, 250/584, 586, 587; 378/147, 154, 19
See application file for complete search history.

(56) References Cited

U.S. PATENT DOCUMENTS

| | | | | |
|---|---|---|---|---|
| 4,496,842 A | * | 1/1985 | Hermens et al. | 250/385.1 |
| 4,521,689 A | * | 6/1985 | Pritzkow | 250/385.1 |
| 4,694,177 A | * | 9/1987 | Akai | 250/368 |
| 4,982,096 A | * | 1/1991 | Fujii et al. | 250/367 |
| 5,510,622 A | * | 4/1996 | Hu et al. | 250/367 |
| 5,592,523 A | * | 1/1997 | Tuy et al. | 378/19 |
| 5,799,057 A | | 8/1998 | Hoffman et al. | |
| 5,965,893 A | | 10/1999 | Tonami et al. | |
| 5,991,357 A | * | 11/1999 | Marcovici et al. | 378/19 |
| 6,134,301 A | | 10/2000 | Mruzek et al. | |
| 6,552,349 B2 | * | 4/2003 | Gagnon et al. | 250/363.1 |
| 6,587,538 B2 | | 7/2003 | Igarashi et al. | |
| 6,658,082 B2 | * | 12/2003 | Okumura et al. | 378/19 |
| 6,760,404 B2 | * | 7/2004 | Saito et al. | 378/98.8 |
| 6,982,423 B2 | * | 1/2006 | Elgali | 250/370.11 |
| 2003/0150994 A1 | * | 8/2003 | Freund et al. | 250/368 |
| 2004/0125915 A1 | * | 7/2004 | Ueno et al. | 378/63 |

FOREIGN PATENT DOCUMENTS

| | | |
|---|---|---|
| DE | 197 27 483 A1 | 1/1998 |
| DE | 197 53 268 A1 | 7/1998 |
| DE | 101 58 021 A1 | 8/2002 |
| GB | 2 034 148 A | 5/1980 |
| JP | 04002989 A | 1/1992 |
| WO | WO 3044563 A1 * | 5/2003 |

* cited by examiner

*Primary Examiner*—David Porta
*Assistant Examiner*—Mark R. Gaworecki
(74) *Attorney, Agent, or Firm*—Harness, Dickey & Pierce, P.L.C.

(57) ABSTRACT

A detector module is proposed for producing an X-ray detector for an X-ray computed tomograph. The module includes a number of detector units, each including sensor elements arranged next to one another in the z-direction and in a phi-direction running perpendicular thereto. The detector units are held on a carrier plate in the manner of a column extending in the z-direction. In order to ensure a precise alignment of the sensor elements, the detector units are positioned on the carrier plate via a collimator element.

21 Claims, 1 Drawing Sheet

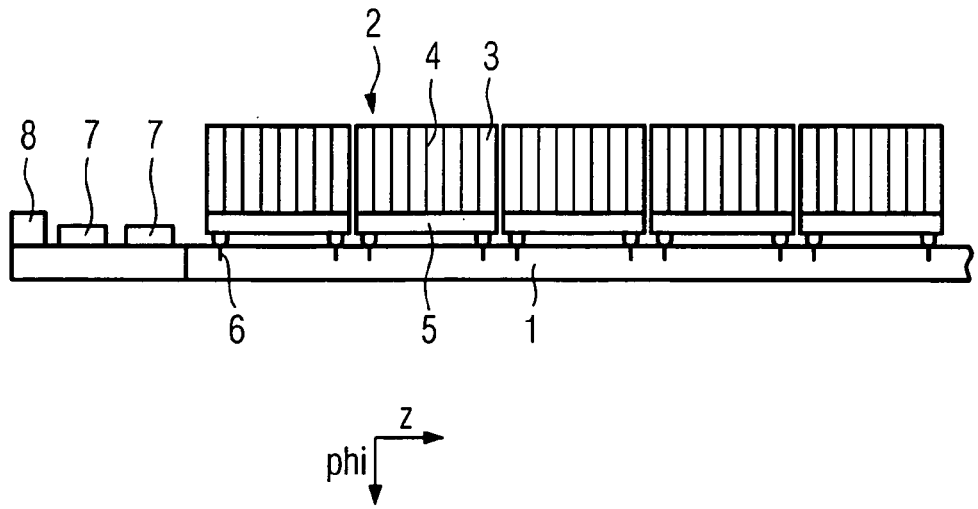
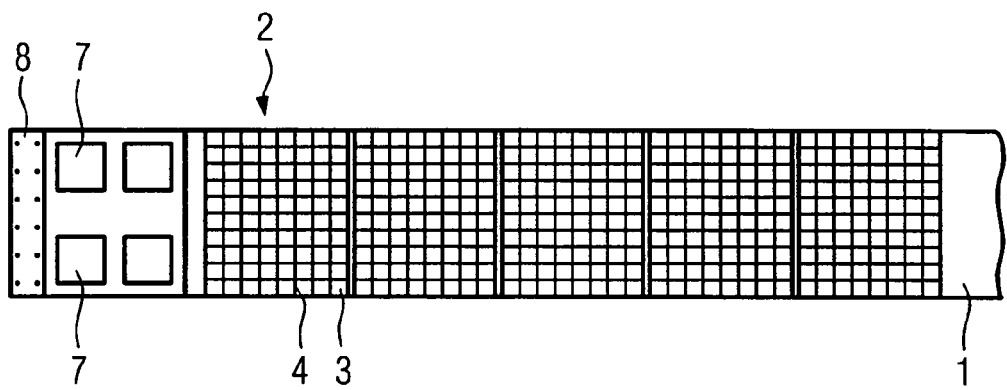
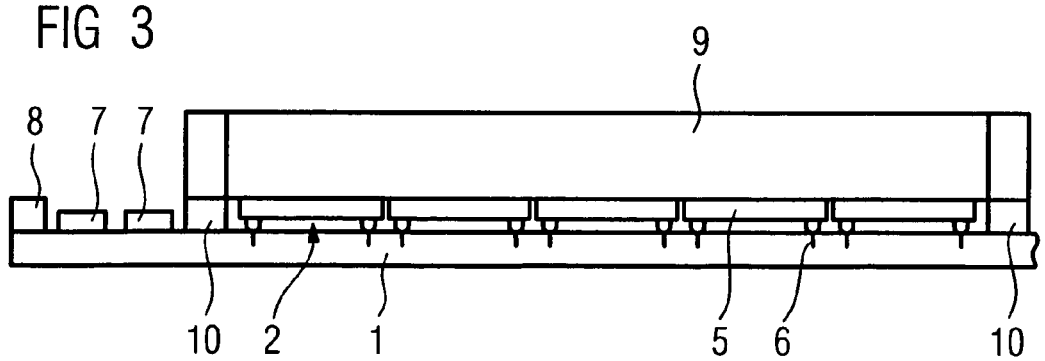

DETECTOR MODULE

The present application hereby claims priority under 35 U.S.C. §119 on German patent application number DE 10 2004 001 688.7 filed Jan. 12, 2004, the entire contents of which are hereby incorporated herein by reference.

FIELD OF THE INVENTION

The invention generally relates to a detector module for producing an X-ray detector for an X-ray computed tomograph.

BACKGROUND OF THE INVENTION

A detector module is known from DE 101 58 021 A1. In order to produce a detector, a multiplicity of such detector modules are fitted next to one another on a frame together with collimator elements matched respectively thereto. In order to bring the individual collimator sheets of the collimator element into alignment with the sensor elements of the detector module, pins are provided on the detector module that engage during mounting in cutouts on the collimator element that correspond thereto. Because of manufacturing tolerances, it can happen that the collimator sheets are not precisely aligned with the sensor elements of the detector modules. Consequently, an undesired measuring inaccuracy can result.

DE 197 53 268 A1 describes a detector for an X-ray computed tomograph. Here, the collimator sheets forming the collimator are adjusted relative to one another by using spacers of comb-like design. The known detector requires a high outlay on production. Again, in this case, there can be an inaccurate alignment of the collimator sheets with reference to sensor elements combined to form detector units.

SUMMARY OF THE INVENTION

It is an object of an embodiment of the invention to reduce or even eliminate at least one of the disadvantages of the prior art. In particular, an object of an embodiment may be to specify a detector module that permits the production of a precise detector, and preferably even as precise a detector as possible for an X-ray computed tomograph. In accordance with a further aim of an embodiment of the invention, the detector module may permit the detector to be mounted as simply and quickly as possible, and/or may be easy to handle.

In accordance with an embodiment of the invention, detector units are positioned on the carrier plate by use of a collimator element. In a departure from the prior art, the collimator element is a constituent of the detector module. An inaccurate alignment is avoided by the collimator module being used for positioning the detector units accurately.

This can be done, for example, by firstly fitting the detector modules on the collimator element. This permits a more exact alignment of the detector modules with reference to the collimator element. Then the detector units may be fixed in their prescribed position on the carrier plate.

The collimator element may be expediently produced from metal sheets extending in the z-direction and/or in the phi-direction. The metal sheets can be held at a prescribed spacing from one another by using suitable spacers that may be produced from plastic, for example.

According to an advantageous refinement, the collimator element may span the detector units like a bridge in the z-direction. It is thereby possible, firstly, to connect the collimator element to the carrier plate and, subsequently, to fix the detector units on the carrier plate with the precise positioning prescribed by the collimator element.

The collimator element may be advantageously connected to the detector units by using an adhesive. This facilitates the handling of the prescribed detector modules.

According to a further refinement, the detector units and the collimator element may be mounted on the carrier plate. The carrier plate can be a printed circuit board. The printed circuit board can be provided with contacts and/or conductor structures for connecting the detector units to a downstream electronic evaluation unit.

According to a further measure, a detector for an X-ray computed tomograph may be provided with a number of detector modules according to an embodiment of the invention, arranged next to one another in the phi-direction. Such a detector can be mounted easily and quickly. In this case, the detector modules can be fitted on a detector frame at a prescribed angle to one another. Mutually corresponding devices for fitting the detector modules on the detector frame in an accurately positioned fashion can be provided on the detector frame and on the detector module. These devices can include, for example, pins and cutouts corresponding thereto.

BRIEF DESCRIPTION OF THE DRAWINGS

An exemplary embodiment of the invention is explained in more detail below with the aid of the drawings, in which:

FIG. 1 shows a side view of a detector module according to an embodiment of the invention, without collimator element, FIG. 2 shows a plan view in accordance with FIG. 1, and FIG. 3 shows a side view of a detector module according to an embodiment of the invention.

DETAILED DESCRIPTION OF THE EXEMPLARY EMBODIMENTS

FIGS. 1 and 2 show a detector module without collimator element. A number of detector elements 2 are held one behind another on a printed circuit board 1 in a column extending in a z-direction. A width of the column in the phi-direction is given in essence by the width of a detector element 2. A length of the column in the z-direction follows from the sum of the lengths of the detector elements 2 arranged one behind another.

Each of the detector elements 2 includes a multiplicity of sensor elements 3. The sensor elements 3 form a matrix that is formed from columns extending in the z-direction, and rows extending in a phi-direction. The detector element 2 advantageously include n×8 sensor elements 3 in the z-direction, and n×8 sensor elements in the phi-direction, n being a whole number. A detector element 2 can thus include 64, 256, etc. sensor elements 3.

The detector elements 2 may be respectively separated from one another by slots 4. The sensor elements 3 can be produced, for example, from a scintillator ceramic such as gadolinium oxysulfide. The sensor elements 3 may be mounted in this case on a photodiode array 5.

On a rear side of the photodiode array 5 that is averted from the sensor elements 3, contact elements 6 may be provided that are connected to conductor tracks or the like (not shown here in more detail). The reference numeral 7 denotes, for example, CMOS modules with the aid of which the signals supplied by the photodiode arrays 5 can be digitized. The reference numeral 8 denotes a plug for connecting a downstream electronic evaluation unit (not shown here).

FIG. 3 shows a schematic side view of a detector module according to an embodiment of the invention. A collimator element 9 may span the detector elements 2 in a fashion similar to a bridge. The collimator element 9 may include collimator sheets (not shown in more detail here) that can be produced from molybdenum, for example. The collimator sheets may be arranged such that they can engage in the slots 4 of the detector elements 2.

In order to ensure an alignment of the sensor elements 3 with reference to the collimator element 9, the detector module according to an embodiment of the invention can be mounted as follows: firstly, the detector units 2 may be plugged into the collimator element 9 such that the collimator sheets engage in the slots 4. This creates a more precise alignment of the sensor elements 3. Subsequently, the cavities remaining between the collimator sheets can be sealed with the aid of a synthetic resin, for example, in order to fix the detector units 2. The compact unit thus formed can then be fastened on the printed circuit board 1 via supports 10 extending from the collimator unit 9. Finally, the contact elements 6 can be brought into contact with conductor tracks provided in the printed circuit board 1.

Such a detector module can be fitted on a frame in order to construct a detector for an X-ray computed tomograph. Cutouts can be provided on the detector module, and pins can be provided on the frame in a conventional manner for the purpose of positioning on the frame. Of course, it is also possible to provide other devices/methods for precise positioning of the detector module on the frame.

The proposed detector modules may be positioned next to one another in the phi-direction on the frame with the aid of the positioning devices, and then fixed. It is particularly easy to mount such a detector. A precise alignment of the sensor elements 3 with reference to the collimator elements 9 may be provided by the proposed detector module.

Exemplary embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A detector module for producing an X-ray detector for an X-ray computed tomograph, comprising:
    a number of detector units, each including a plurality of sensor elements arranged next to one another in a first direction and in a second direction perpendicular to the first direction, the plurality of sensor elements being separated by slots;
    a carrier plate adapted to hold the detector units in a column extending in the first direction; and
    a collimator element including a plurality of collimator sheets;
    wherein the collimator element is adapted to precisely position the detector units on the carrier plate in that the collimator sheets engage in the slots.

2. The detector module as claimed in claim 1, wherein the collimator element is produced from metal sheets extending in at least one of the first and second directions.

3. The detector module as claimed in claim 2, wherein the collimator element is connected to the detector units via an adhesive.

4. The detector module as claimed in claim 2, wherein the detector units and the collimator element are mounted on the carrier plate.

5. The detector module as claimed in claim 2, wherein, for each of the detector units, an integral multiple of eight sensor elements are arranged next to one another in at least one of the first and second directions.

6. The detector module as claimed in claim 2, wherein the metal sheets are held at a prescribed spacing from one another by using suitable spacers.

7. The detector module as claimed in claim 6, wherein the spacers are produced from plastic.

8. The detector module as claimed in claim 1, wherein the collimator element spans the detector units in the first direction.

9. The detector module as claimed in claim 1, wherein the collimator element is connected to the detector units via an adhesive.

10. The detector module as claimed in claim 1, wherein the detector units and the collimator element are mounted on the carrier plate.

11. The detector module as claimed in claim 10, wherein the carrier plate is a printed circuit board.

12. The detector module as claimed in claim 1, wherein, for each of the detector units, an integral multiple of eight sensor elements are arranged next to one another in at least one of the first and second directions.

13. A detector for an X-ray computed tomograph including a number of detector modules, arranged next to one another in the second direction, as claimed in claim 1.

14. The detector as claimed in claim 13, wherein the detector modules are fitted on a detector frame at a prescribed angle to one another.

15. The detector as claimed in claim 14, wherein mutually corresponding devices, for fitting the detector modules on the detector frame in an accurately positioned fashion, are provided on the detector frame and on the detector module.

16. The detector as claimed in claim 13, wherein mutually corresponding devices, for fitting the detector modules on the detector frame in an accurately positioned fashion, are provided on the detector frame and on the detector module.

17. A detector module for producing an X-ray detector for an X-ray computed tomograph, comprising:
    a number of detector units, each including a plurality of sensor elements arranged next to one another in a first direction and in a second direction perpendicular to the first direction;
    a carrier plate adapted to hold the detector units in a column extending in the first direction; and
    a collimator element adapted to precisely position the detector units on the carrier plate,
    wherein the carrier plate is a printed circuit board.

18. A detector for an X-ray computed tomograph, comprising:
    a plurality of detector modules, arranged next to one another, wherein each of the detector modules includes,
    a plurality of detector units, each including a plurality of sensor elements that are separated by slots;
    a carrier plate adapted to hold the detector units in a column; and
    a collimator element including a plurality of collimator sheets;
    wherein the collimator element is adapted to precisely position the detector units on the carrier plate in that the collimator sheets engage in the slots.

19. The detector as claimed in claim 18, wherein the detector modules are fitted on a detector frame at a prescribed angle to one another.

20. The detector as claimed in claim 19, wherein mutually corresponding devices, for fitting the detector modules on the detector frame in an accurately positioned fashion, are provided on the detector frame and on the detector module.

21. A detector module for producing an X-ray detector for an X-ray computed tomograph, comprising:

a number of detector units, each including a plurality of sensor elements arranged next to one another in a first direction and in a second direction perpendicular to the first direction, the plurality of sensor elements being separated by slots;

a carrier plate adapted to hold the detector units in a column extending in the first direction; and a collimator element including a plurality of collimator sheets, wherein the collimator sheets are configured to insert into the slots between the plurality of sensor elements of the detector units.

* * * * *